(12) United States Patent
Geurts et al.

(10) Patent No.: US 6,888,136 B2
(45) Date of Patent: May 3, 2005

(54) METHOD OF OBTAINING A PARTICLE-OPTICAL IMAGE OF A SAMPLE IN A PARTICLE-OPTICAL DEVICE

(75) Inventors: Remco Theodorus Johannes Petrus Geurts, Oss (NL); Michael Frederick Hayles, Eindhoven (NL)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 10/653,735

(22) Filed: Sep. 2, 2003

(65) Prior Publication Data

US 2004/0041094 A1 Mar. 4, 2004

(30) Foreign Application Priority Data

Sep. 2, 2002 (NL) .............................................. 1021376

(51) Int. Cl.[7] .................................................. G21K 5/08
(52) U.S. Cl. ...................... 250/307; 250/309; 250/310; 250/443.1
(58) Field of Search ................................. 250/307, 309, 250/310, 311, 441.11, 443.1

(56) References Cited

U.S. PATENT DOCUMENTS

| | | | | |
|---|---|---|---|---|
| 3,761,709 A | * | 9/1973 | Hasegawa et al. | 250/442.11 |
| 4,284,894 A | * | 8/1981 | Sitte et al. | 250/443.1 |
| 4,591,722 A | * | 5/1986 | Biddlecombe et al. | 250/443.1 |
| 4,749,868 A | * | 6/1988 | Hatanaka et al. | 250/443.1 |
| 4,916,314 A | * | 4/1990 | Smith | 250/307 |
| 5,274,237 A | * | 12/1993 | Gallagher et al. | 250/370.15 |
| 5,986,270 A | * | 11/1999 | Bormans et al. | 250/442.11 |

OTHER PUBLICATIONS

Scale–Space Signatures for the Delection of Clustered Microcalcifications In Digital Mammograms, IEEE Transactions on Medical Imaging vol. 18, No. 9, Sep. 1999, pp. 774–786.

\* cited by examiner

*Primary Examiner*—Nikita Wells
*Assistant Examiner*—Anthony Quash
(74) *Attorney, Agent, or Firm*—Michael D. Scheinberg

(57) ABSTRACT

In relatively thick samples for electron microscopy imaging, details of interest are often located in the bulk of the sample, so that they cannot be directly imaged in the form of a SEM image. According to the invention, so as to expose the cross-section containing the details of interest, the frozen sample is subjected to ion milling, in such a manner that the desired cross-section is exposed. Thereafter, the exposed cross-section is further eroded in a controlled manner via sublimation, whereby the detail of interest is approached in a very accurate manner, and its fine details become visible. Hereafter, the finally desired SEM image can be made. By repetition of this process, a large number of successive cross-sections can be imaged, so that a spatial representation of the sample is obtained.

7 Claims, 2 Drawing Sheets

METHOD OF OBTAINING A PARTICLE-OPTICAL IMAGE OF A SAMPLE IN A PARTICLE-OPTICAL DEVICE

FIELD OF THE INVENTION

The invention relates to method of obtaining a particle-optical image of a sample in a particle-optical device. The invention also relates to a particle-optical device embodied to perform the method.

BACKGROUND OF THE INVENTION

When using relatively thick samples (i.e. with a thickness of the order of 0.1 mm) in particle-optical devices such as electron microscopes, one can be confronted with the problem that the details to be studied in the sample are located on the interior of the material of the sample. Such a situation can, for example, arise when using a bacterium as a sample, whereby one would like to subject a detail to further analysis using a (much) stronger magnification in the electron microscope. The device user may suspect that a detail that is of possible interest is situated at a given location on the interior of the sample, but this detail is buried in the bulk of the material and is thus out of the reach of electron-optical imagery using, for example, a Scanning Electron Microscope (SEM). One could conceive, in a separate operation outside the electron microscope, attempting to open up the sample in such a manner that the detail of interest becomes exposed, but, because the detail involved is often smaller than the wavelength of visible light, the processing thereof is obscured from direct observation by the person performing the processing, so that, in the exposure attempt, the detail of interest can easily be missed, or exposed in an undesirable manner. Moreover, it is extremely difficult, and often impossible, to find the right location in which to make a cross-section.

SUMMARY OF THE INVENTION

The invention strives to provide a solution to the above-mentioned problem using a method on the basis of which, in a controlled manner, a cross-section of the sample is exposed, in which cross-section the detail of interest is located, in such a manner that this detail becomes accessible to electron-optical imagery. To this end, the method according to the invention has the following successive steps:

the sample, which has been put in a frozen state, is subjected in a vacuum environment to a milling operation using an ion beam, whereby, in the vacuum environment, a cooled opposing surface has been provided, the temperature of the frozen sample being higher than that of the opposing surface, said milling operation causing a pre-selected cross-section of the sample to be exposed;

the temperature difference between the sample and the opposing surface is increased, which increase of the temperature difference leads to sublimation of the exposed cross-section of the sample;

an image of at least a portion of the exposed cross-section of the sample is made with the aid of a scanning focused electron beam.

The sample can be put in a frozen state by first saturating it with a liquid, and subsequently cooling it to a temperature below the freezing point of the liquid. By freezing the sample, one achieves the creation of a completely filled matrix, as a result of which, during further processing, all portions of the detail of interest in the sample remain in their original positions, and do not change in form or structure. To achieve this, the sample is frozen at high speed.

After it has been determined in which region of the sample the detail of interest is located—by studying a free surface of the frozen sample, or by using some other method—the region concerned is subjected to a milling operation with an ion beam, with the aim of exposing the detail of interest and, thus, making it accessible to SEM imagery. This milling operation occurs in a vacuum environment, i.e. an environment with a low pressure, typically 10-6 mbar. A cooled opposing surface is provided in the vacuum environment, to bind the molecules that evaporate out of the filled matrix. To make such binding possible, the temperature of the opposing surface is lower than that of the sample, e.g. 20° C. lower. The opposing surface can have the form of a cooling finger that is held at the desired temperature using, for example, liquid nitrogen. The milling procedure can be manually controlled by the user, or can be controlled by computer.

Once the region containing the detail of interest is exposed by the milling process, the detail of interest is made further accessible to SEM imagery at relatively low speed. This occurs because the temperature difference between the sample and the opposing surface is increased, e.g. because the temperature of the sample is increased. As a result of this, sublimation occurs of the frozen liquid in the exposed cross-section of the sample. As a result of the relatively low speed of sublimation, it is possible for the user to expose the desired detail with a high degree of accuracy, and to subsequently image it. This imaging occurs with the aid of a scanning focused electron beam (SEM imaging) so as to prevent an eroding action of the imaging beam on the detail of interest. Moreover, by choosing the position of the opposing surface, one can determine the position on the sample from which sublimation is to occur. This is because the region from which the greatest sublimation occurs is the region located nearest to the opposing surface. Therefore, by placing the opposing surface proximate to th desired region, sublimation in that region can be achieved.

In a preferential embodiment of the invention, the milling operation with an ion beam is observed by imaging at least a part of the exposed cross-section of the sample with the aid of a scanning focused electron beam. In this manner, the user can monitor the milling process in detail and, if desired, stop milling once the process has achieved the desired degree of progress.

In another preferential embodiment of the invention, the sublimation process is observed by imaging at least a part of the exposed cross-section of the sample with the aid of a scanning focused electron beam. In this way, just as in the case of the milling process, the user can monitor the sublimation process in detail and, if desired, stop the process once it has achieved the desired degree of progress.

In yet another preferential embodiment of the invention, the sample to be frozen contains water. The advantage of water is that this liquid is already naturally present in many specimens, such as in biological specimens, for example. If water is not already present in the sample, it can be saturated with water prior to the freezing process. Water that is released during the milling process and the sublimation process can be easily bound to the opposing surface at lower temperature.

In another embodiment of the invention, the ion beam is a focused ion beam. By focusing the ion beam, it is possible, in a very precise manner, to define the region that is to be milled and, if desired, to endow it with all sorts of special forms, whereby the milling process becomes controllable to a high degree.

In yet another embodiment of the invention, the ions in the ion beam are heavier than oxygen atoms. As a result of the relatively large mass of the ions, oxygen atoms in the water (or another matrix liquid, such as alcohol) are easily knocked out of places as a result of which a high-speed milling process is achieved.

In yet another embodiment of the invention, the speed of sublimation is regulated by varying the solid angle at which the cooled opposing surface is seen from the sample. This embodiment is of advantage when, for example, liquid nitrogen is used to cool the opposing surface. The temperature of the opposing surface is then determined by the boiling point of the nitrogen, and is therefore not easy to regulate. By displacing the opposing surface toward or away from the sample, said solid angle is varied, along with the number of captured water molecules and, consequently, the speed of sublimation. In this manner, an accurate regulation of this speed becomes possible.

In yet another embodiment of the invention, after performing imaging with the aid of a scanning focused electron beam, an ion milling process and a sublimation process are performed anew, after which imaging of at least a portion of the newly exposed cross-section of the sample thus obtained is performed anew with the aid of a scanning focused electron beam. In this manner, it is possible to make a series of SEM images with a steadily (somewhat) advanced erosion front whereby the time between two consecutive images is short as a result of the relatively high speed of the ion milling process, and the distance between two imaging cross-sections can be determined extremely accurately as a result of the high accuracy of the milling process and the sublimation process. In this manner, a three-dimensional re-construction can be made with SEM images.

BRIEF DESCRIPTION OF THE DRAWINGS

The invention will be described with the aid of figures, whereby identical reference numerals indicate corresponding parts. In the figures.

DETAILED DESCRIPTION

Figure 1:
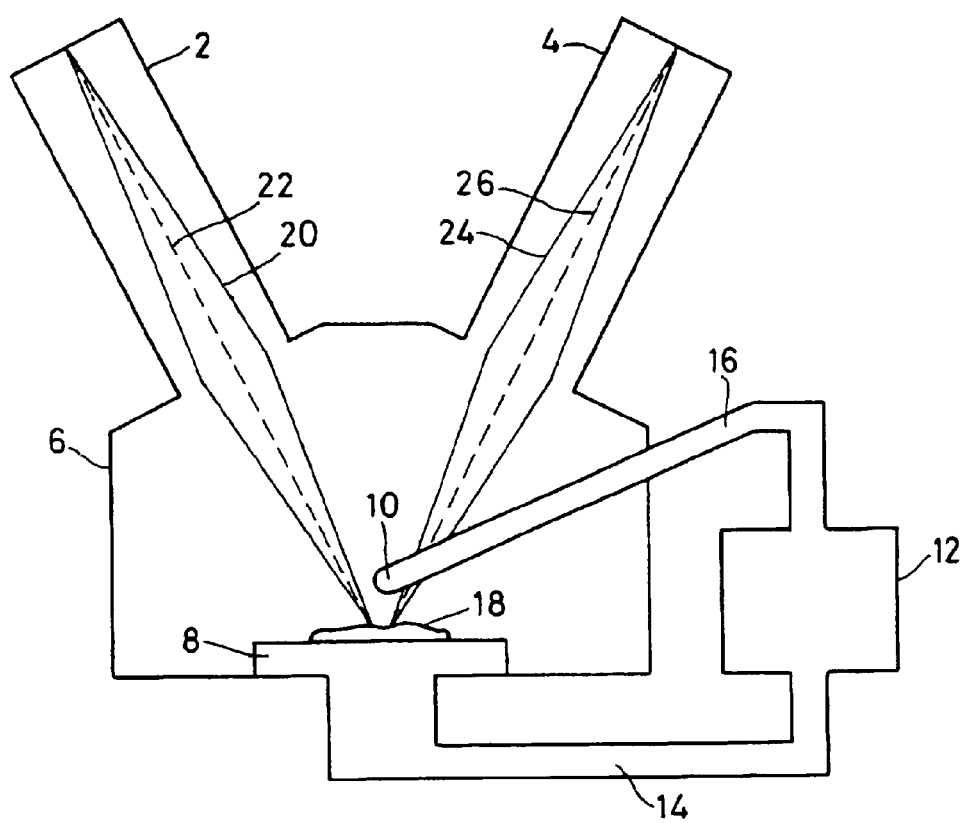
FIG. 1 shows, in schematic form, a particle-optical device for performing the method according to the invention.

FIG. 1 schematically depicts a particle-optical device for performing the method according to the invention. The device is formed by a so-called Dual Beam system, in which two particle-optical columns 2 and 4 are present, whereby column 2 is an ion-optical column and column 4 is an electron-optical column. Both columns 2 and 4 are mounted to a sample space 6 that can be evacuated and in which a sample stage 8 is present. The sample space 6 is also provided with a cooled opposing surface in the form of a cooling finger 10. The sample stage 8 and the cooling finger 10 can be adjusted to a desired low temperature by means of a schematically depicted cooling installation 12. The connection between the cooling installation 12 and the sample stage 8 is schematically depicted by cooling duct 14, and that between the cooling installation 12 and the cooling finger 10 by cooling duct 16. The sample 18 that is to be processed is located on the sample stage.

Column 2 produces an ion beam 20 that proceeds along an optical axis 22; this ion beam 20 is focused onto the sample 18 using particle-beam lenses (not depicted). With the aid of (non-depicted) scanning coils, the focused ion beam 20 can execute a desired scanning pattern upon a portion of the sample 18 that is to be processed using this ion beam. Column 4 produces an electron beam 24 that proceeds along an optical axis 26: this electron beam 24 is focused onto the sample 18 using particle-beam lenses (not depicted). In addition, column 4 is provided in a known manner with (non-depicted) scanning coils, in such a fashion that, in a known manner, a SEM image can be obtained of the region of the sample 18 that is to be processed and/or imaged.

The sample 18 is introduced into the sample space 6 in a frozen state and is held there at a desired low temperature with the aid of the cooling installation 12, which cools the sample stage 8. It is also possible to place the sample on the sample stage 8 in a non-frozen state, and to subsequently freeze the sample in situ. So as to ensure that the structure of the sample is not adversely affected by the freezing procedure, one must ensure a sufficiently high rate of freezing, e.g. 105 K/s. It is assumed that the sample prior to being frozen was saturated with water, such that, after being frozen, the sample consists of the sample material embedded in a matrix of ice. The temperature at which the sample is processed depends on the application; for example, the temperature is that of liquid nitrogen, which is approximately −196° C. The cooling finger 10 is placed opposite the sample 18, which finger is also maintained at a desired low temperature with the aid of cooling installation 12. The temperature of the cooling finger 10 can deviate from the temperature of the sample 18, as will be further explained hereunder.

Figure 2A:
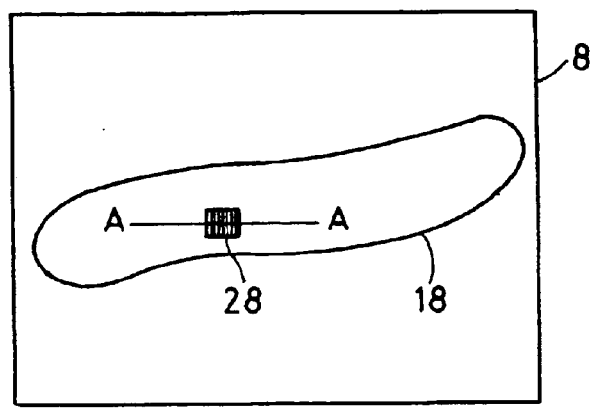
FIG. 2A renders a depiction of a sample to be processed according to the invention.
Figure 2B:
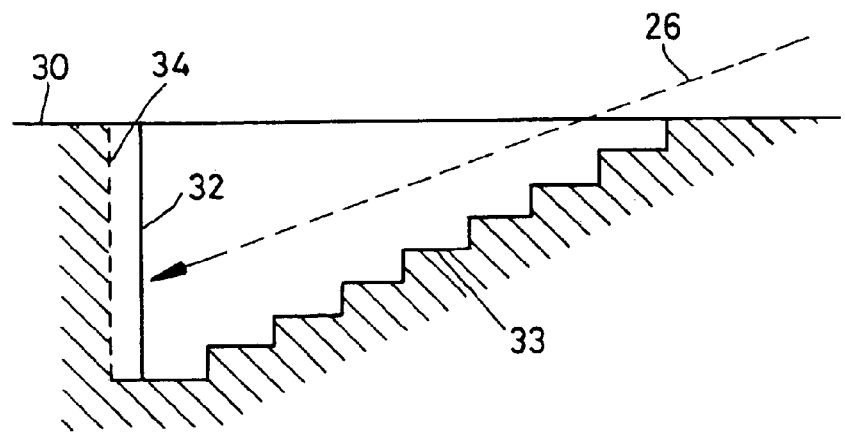
FIG. 2B shows a transverse cross-section along the line A—A in FIG. 2A in the sample to be processed according to the invention.

The milling process of the sample 18 will be further elucidated on the basis of FIGS. 2A and 2B. FIG. 2A renders a plan view of the sample stage 8 with the sample 18. The processing of the sample according to the invention begins with the selection of a region 28 of the sample, in which region the user suspects a detail of interest to be located. Subsequently, this region is subjected to a milling process with the ion beam 20, with the aim of exposing a cross-section in which the detail of interest is located. The ions in the ion beam 20 are, for example, gallium ions, argon ions or other ions with an atomic mass that (greatly) exceeds that of oxygen. The effect of this choice is that the milling process occurs at relatively high speed, because the oxygen atoms of the matrix are easily knocked out of place by the much heavier ions. During milling, the temperature of the sample is typically of the order of magnitude of −130° C., and the temperature of the cooling finger is typically of the order of magnitude of −150° C. The distance from the tip of the cooling finger to the sample is typically 5 mm. As a result of the presence of the cooling finger, the water released during the milling process is bound to the cooling finger, thus preventing water molecules knocked out of place by the ions from returning again to the sample and disturbing or slowing down the milling process there. A typical value for the energy of the ions during the milling process is of the order of magnitude of 30 to 50 keV for fast milling; for finer processing applied when approaching the detail of interest, a typical value is 5 keV. A typical value for the current in the ion beam is of the order of magnitude of 1–50 nA. During the milling process, the pressure in the vacuum environment is typically of the order of magnitude of 10-6 mbar. During the milling operation, the process is monitored by means of SEM imagery with the aid of the electron beam 24.

In FIG. 2A, the line AA indicates a transverse cross-section of the cavity formed using the milling procedure.

FIG. 2B shows this transverse cross-section. In FIG. 2B, the upper surface of the sample is indicated by numeral 30. The focused ion beam is scanned over the surface of the region that has been selected for milling, whereby a portion of the volume of the cavity is continually removed. A side wall 32 of the cavity constitutes the cross-section of the sample that is to be exposed and that contains the detail of interest. The cavity has such a form that it is possible to make a SEM image of the exposed surface 32. To this end, sufficient material is removed to enable the electron beam (which, in this figure, is symbolically depicted by the optical axis 26) to irradiate the surface to be imaged at an angle that enables imaging, however, the milling away of more material than is necessary to make the SEM image is avoided. It is for this reason that the wall 33 of the cavity demonstrates the depicted slanted progression.

When, on the basis of the SEM images made during the milling process, one concludes that the milling process has advanced to a sufficient degree, the milling process is stopped and the sublimation phase can begin. The sublimation phase is commenced by increasing the temperature difference between the cooling finger and the sample; in the numerical example used here, the temperature of the sample is increased from $-130°$ C. to $-95°$ C., while the temperature of the cooling finger stays the same. The sublimation causes the removal of material from the surface to proceed much more slowly, thus achieving an extremely controlled progression of the exposure of the detail of interest. Also, in this manner, all sorts of very fine details are exposed, because only the ice matrix evaporates and the surrounding portions of the sample are preserved, since these are no longer subjected to ion bombardment during the sublimation phase. The sublimation phase can also be followed with the aid of SEM images until the detail of interest is exposed in such a manner that the finally desired SEM image can be made. If desired, it is possible to repeat the process, i.e. ion milling is used to remove so much material from the wall 32 that a new wall 34 arises, after which yet another sublimation phase is initiated, a finally desired SEM image is made, and further repetition is possible. In this manner, by making a large number of SEM images of successive cross-sections, one can obtain a three-dimensional representation of the interior of the sample. In this way, the entire process occurs in one and the same particle-optical device, so that introduction into and removal out of vacuum between the SEM images is rendered unnecessary, whereby a substantial saving in time can be realized.

Figure 3:
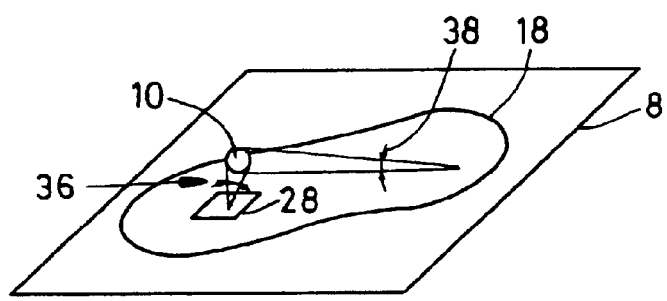
FIG. 3 gives an illustration of the effect of the solid angle at which the opposing surface is seen from the sample.

FIG. 3 illustrates the influence of the position of the cooling finger 10 with respect to the region 28 of interest in the sample 18. Because the cooling finger (which, in this figure, is schematically depicted by its tip 10) is located in the direct vicinity of the region 28, the sublimation will predominantly occur from said region. This is caused by the fact that the cooling surface, viewed from this region, subtends a relatively large solid angle, which is clearly larger than the subtended solid angle 38 when the cooling surface is viewed from a remote region of the sample.

What is claimed is:

1. Method for obtaining a particle-optical image of a sample in a particle-optical device, in which, successively: the sample which has been put in a frozen state, is subjected in a vacuum environment to a milling operation using an ion beam, a cooled surface opposing the sample surface has been provided in the vacuum environment, the temperature of the frozen sample being higher than that of the opposing surface, said milling operation causing a pre-selected cross-section of the sample to be exposed; the temperature difference between the sample and the opposing surface is increased, which increase of the temperature difference leads to sublimation of the exposed cross-section of the sample; creating an image during the sublimation process of at least a part of the exposed cross-section of the sample with the aid of a scanning focused electron beam.

2. Method according to claim 1 in which the milling operation with an ion beam is observed by imaging at least a part of the exposed cross-section of the sample with the aid of a scanning focused electron beam.

3. Method according to claim 1 in which the sample to be frozen contains water.

4. Method according to claim 1 in which the ion beam is a focused ion beam.

5. Method according to claim 1 or 4 in which the ions in the ion beam are heavier than oxygen atoms.

6. Method according to claim 1 in which the speed of sublimation is regulated by varying the solid angle at which the cooled opposing surface is seen from the sample.

7. Method according to claim 1 in which, after performing imaging with the aid of a scanning focused electron beam, an ion milling process and a sublimation process are performed anew, after which imaging of at least a portion of the newly exposed cross-section of the sample thus obtained is performed anew with the aid of a scanning focused electron beam.

* * * * *